United States Patent
Schmidt et al.

(10) Patent No.: US 9,366,378 B2
(45) Date of Patent: Jun. 14, 2016

(54) SUPPORT ARM FOR ULTRASOUND SCANNING

(75) Inventors: Martin Schmidt, Emskirchen (DE); Satchi Panda, Fremont, CA (US); Todd Pleake, Sammamish, WA (US)

(73) Assignees: Siemens Medical Solutions USA, Inc., Malvern, PA (US); Siemens Aktiengesellschaft, München (DE)

( * ) Notice: Subject to any disclaimer, the term of this patent is extended or adjusted under 35 U.S.C. 154(b) by 687 days.

(21) Appl. No.: 12/369,177

(22) Filed: Feb. 11, 2009

(65) Prior Publication Data

US 2010/0204578 A1  Aug. 12, 2010

(51) Int. Cl.
*A61B 8/14* (2006.01)
*F16M 11/24* (2006.01)
*A61B 8/00* (2006.01)
*F16M 11/04* (2006.01)
*F16M 11/14* (2006.01)
*F16M 11/20* (2006.01)

(52) U.S. Cl.
CPC .............. *F16M 11/24* (2013.01); *A61B 8/4218* (2013.01); *A61B 8/4281* (2013.01); *F16M 11/04* (2013.01); *F16M 11/14* (2013.01); *F16M 11/2014* (2013.01); *F16M 11/2092* (2013.01); *F16M 2200/044* (2013.01); *F16M 2200/063* (2013.01)

(58) Field of Classification Search
CPC .............. A61B 2019/5229; A61B 2019/5276; A61B 8/4281; F16M 11/04; F16M 11/14; F16M 11/2014; F16M 11/2092; F16M 11/24; F16M 2200/044; F16M 2200/063
See application file for complete search history.

(56) References Cited

U.S. PATENT DOCUMENTS

| | | | | |
|---|---|---|---|---|
| 4,291,578 A | * | 9/1981 | Hetz et al. | 73/633 |
| 6,129,319 A | * | 10/2000 | Metelski | 248/123.2 |
| 7,862,512 B2 | | 1/2011 | Iikubo et al. | |
| 7,993,289 B2 | | 8/2011 | Quistgaard et al. | |
| 8,229,021 B2 | | 7/2012 | Miyazaki et al. | |
| 2002/0064048 A1 | * | 5/2002 | Sander | 362/401 |
| 2004/0263102 A1 | * | 12/2004 | Kraus et al. | 318/432 |
| 2005/0166413 A1 | * | 8/2005 | Crampton | 33/503 |
| 2005/0193451 A1 | * | 9/2005 | Quistgaard et al. | 901/9 |

FOREIGN PATENT DOCUMENTS

| | | | |
|---|---|---|---|
| JP | 54086984 A | | 7/1979 |
| JP | 2274482 A | | 11/1990 |
| JP | 06070927 A | | 3/1994 |

(Continued)

OTHER PUBLICATIONS

U-Systems Healthcare Professionals, somo•v, Automated Breast Ultrasound View with Somo.v, Jan. 12, 2009, http://www.u-systems.com/Healthcare_Professionals/index.cfm/13.

(Continued)

*Primary Examiner* — Katherine Fernandez
*Assistant Examiner* — Farshad Negarestan
(74) *Attorney, Agent, or Firm* — Lempia Summerfield Katz LLC

(57) ABSTRACT

A transducer connects with a support arm. The support arm supports only some of the weight, even in a locked state. By only supporting a portion or less than all of the weight, the support arm allows downward movement or pressure, but less than the pressure applied without any resistance for the gravity acting on the support arm. The pressure maintains contact between the patient and the transducer for scanning.

12 Claims, 2 Drawing Sheets

(56) References Cited

FOREIGN PATENT DOCUMENTS

| | | |
|---|---|---|
| JP | 2005224921 A | 8/2005 |
| JP | 2007090049 A | 4/2007 |
| JP | 2007516806 A | 6/2007 |
| JP | 2007534448 A | 11/2007 |
| JP | 2008036283 A | 2/2008 |
| WO | WO 2007/014292 A2 | 2/2007 |

OTHER PUBLICATIONS

Chinese Office Action dated Jan. 7, 2013 for corresponding Chinese Patent Application No. 201010117689.8 with English translation.
Chinese Office Action dated Jul. 12, 2013 for corresponding Chinese Patent Application No. 201010117689.8 with English translation.
Japanese Office Action dated Dec. 16, 2013 for corresponding Japanese Patent Application No. 2010-028500 with English translation.

* cited by examiner

SUPPORT ARM FOR ULTRASOUND SCANNING

BACKGROUND

The present embodiments relate to a support arm for ultrasound scanning. For scanning with ultrasound, a sonographer holds a transducer probe at the desired position. However, holding the transducer probe may be difficult due to weight strain, uncomfortable positioning of the sonographer, or distraction from viewing an image.

Robotic or other support arms may be used to assist the sonographer. For example, a scissor arm structure holds a transducer probe adjacent a patient for a volume scan. Frictional engagement or other resistance in the scissor arm structure brings about an approximate equilibrium in terms of weight. Using handles on the transducer probe, the sonographer positions the transducer probe adjacent to the patient, such as over a breast. Once positioned, the sonographer initiates the ultrasound scan. A volume of the patient is scanned. For a successful scan, contact between the transducer probe and the patient is maintained. sonographer apply pressure

BRIEF SUMMARY

By way of introduction, the preferred embodiments described below include a method, systems, transducers, and stands for ultrasound scanning. A transducer connects with a support arm. The support arm supports only some of its weight during scanning, even in a locked state. The support arm may or may not be neutrally buoyant or at equilibrium during positioning, but is not in equilibrium during scanning. By only supporting a portion or less than all of the weight during scanning, the support arm allows downward movement or pressure, but less than the pressure applied without any resistance for the gravity acting on the support arm.

In a first aspect, a system is provided for ultrasound scanning. At least a first support arm connects with an ultrasound transducer. The support arm is moveable. A resistance device is configured to counteract more or less than all of a force from gravity applied to the first support arm, such that gravity causes the ultrasound transducer to press against an object for scanning but with a pressure less than caused by the force from gravity applied to the first support arm without the resistance device.

In a second aspect, a method is provided for supporting an ultrasound transducer. At least one brake is arranged to lock an ultrasound transducer support structure in a position to scan a patient. At least one portion of the ultrasound transducer support structure is allowed to move along at least one dimension while the ultrasound transducer support structure is locked. A resistance to gravity in the one portion is mistuned such that the portion presses against the patient due to gravity.

In a third aspect, a system is provided for ultrasound scanning. A plurality of links is movable relative to each other. An ultrasound probe connects with a first one of the plurality of links. A first link holder is operable to maintain a second one or the first one of the links in a stable position. A second link holder is configured to allow downward motion and resist motion of the second one or the first one of the links different than the link maintained by the first link holder. An adjustable force applicator is configured to alter an amount of resistance to the motion of the second link holder.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Instead of using a support system maintained at equilibrium with gravity, non-equilibrium is used. Non-equilibrium is provided just during scanning, but may be provided at other times (e.g., during positioning or after use to clear from a patient). Spring or gas spring systems counter some but not all of the weight. The moving shafts may be blocked or braked. A pivot shaft or lifting shaft in the overall system is not braked. Not braking one or more shafts allows, by an intentional lack of equilibrium, exertion of a certain additional contact pressure on the object. The contract pressure is provided without user-applied pressure. This may increase coupling of the object to the ultrasound head.

The partial support, such as for one shaft with full equilibrium for the other shafts, allows for easy sonographer positioning. The support structure counters some or all of the weight during positioning. Once positioned for scanning, the position desired by the sonographer is assured during the measurement process by locking the support structure. Incorrect measurements from a change of location or tilting during the measurement are avoided. By the mistuning of the weight equilibrium in one axis (e.g., vertical), the weight of the system itself (e.g., one or more arms, any monitor, and the transducer probe) may be utilized to press the transducer probe against the object being scanned. The system has freedom to apply the designed or desired pressure on the object while the object moves, such as movement due to breathing.

Figure 1:
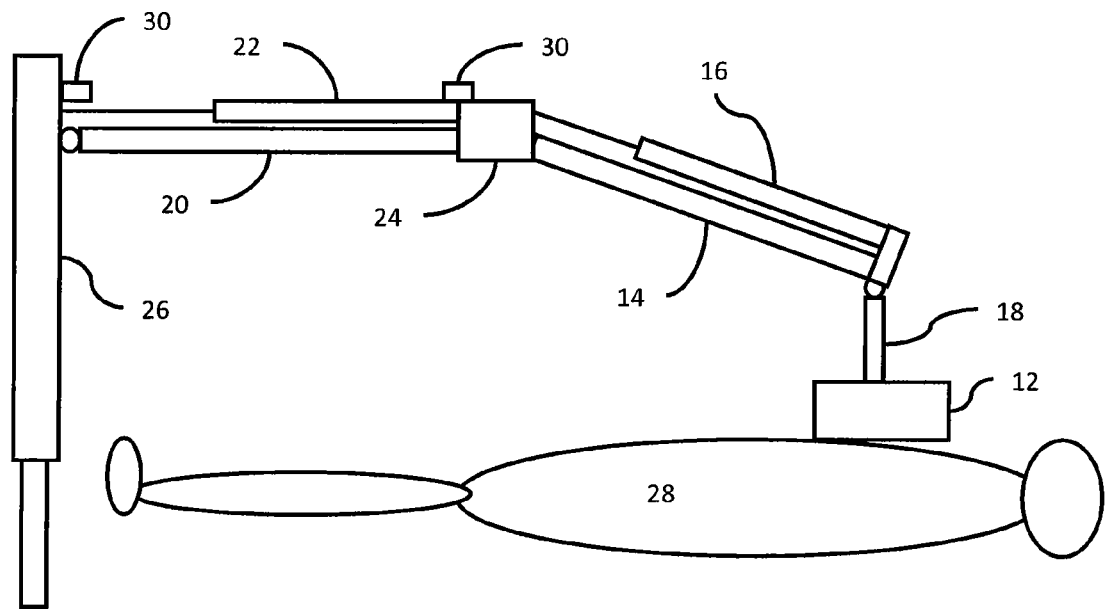
FIG. 1 illustrates one embodiment of a system for ultrasound scanning.

FIG. 1 shows one embodiment of a system for ultrasound scanning. The system is for breast scanning, but may be used for other types of scans. The system includes a support arm structure, such as the ultrasound transducer 12, arms 14, 18, 20, 26, brakes 30, resistance devices 16, 22, and hinge 24. For ease of reference, some repetitive components are not shown, such as a resistance device in or on the arm 26, brakes at other joints than between the arms 14, 20, and hinges 24 at other joints than between the arms 14, 20. Additional, different, or fewer components may be provided. For example, any number of arms 14, 18, 20, 26 is provided, such as only one, only two, only three or more than four. As another example, the brake 30 is part of the resistance device 22. In another example, an ultrasound imaging system is adjacent to or connects with the support structure.

The ultrasound transducer 12 is an array of transducer elements in a probe housing. The elements are arranged as a one or two-dimensional array of elements. Electronic or mechanical steering for the elements may be used. For example, the array is a wobbler array. As another example, the array is a two-dimensional array. The array is flat or curved.

The housing may or may not have handles for positioning the ultrasound transducer 12 at a desired location. The housing includes a bladder. The bladder connects to a bottom side for positioning between the patient and the array. The bladder is liquid filed, such as a liquid with little acoustic attenuation or similar acoustic impedance as the patient. The bladder conforms to the contours of the patient while providing an acoustic path from the array to the patient. In alternative embodiments, a bladder is not provided. Acoustic contact is provided by application of a gel to the patient or the ultrasound transducer 12. A membrane may be used instead of a bladder.

The ultrasound transducer 12 connects with the support arms 14, 18, 20, and 26. The transducer 12 directly connects with the support arm 18. The transducer 12 may directly connect with different or additional support arms 14, 18, 20, or 26. The connection is a ball and socket, allowing relative swiveling of the ultrasound transducer 12 about the support arm 18. Alternatively, the connection is hinged or other rotatable, extendable, or moveable connection. The connection may include a brake, such as a detent structure, pin, brake pad, or other device for releasably locking the ultrasound transducer 12 at a position relative to the support arm 18. In other embodiments, the connection is fixed, not allowing relative motion of the support arm 18 and the ultrasound transducer 12.

The support arms 18, 14, 20, and 26 are metal, plastic, fiberglass, wood, combinations thereof, or other materials. The support arms 18, 14, 20, and 26 have any length, shape, or size. For example, the support arm 18 is a tubular link having a relatively short length. As another example, the support arms 14 and 20 have square or rectangular cross-sections with or without a hollow interior. In another example, the support arm 26 is formed from nested cylinders. The support arms 14, 18, 20, 26 are links having the same or different construction. The support arms 14, 18, 20, 26 may be the same or different from each other. Any combination of types of support arms may be used.

The hinge 24 is a ball and socket, folding hinge, straight hinge, or other joint for connecting the links. For example, the hinge 24 is a plate with four holes, allowing pivoting connection with the support arms 14, 20 and the corresponding resistance devices 16, 22. In other embodiments, the hinge 24 is formed by the connection of two or more support arms 14, 18, 20, 26, such as a pin extending through holes in two support arms 14, 20.

The hinge 24 and support arms 14, 18, 20, 26 allow relative motion. The motion may be rotation about an axis of the link, may be rotation of one link at an angle to another link (e.g., hinged), and/or extension or contraction along the axis of a link. In one embodiment, the support structure allows positioning of the ultrasound transducer 12 in any position within a volume around a base of the support structure. One or more of the support arms 14, 18, 20, 26 are moveable in an up and down (e.g., vertical) direction. Motion in other directions may alternatively or additionally be provided.

The support structure, such as the support arm 20, mounts to another structure. For example, the support arm 20, without the arm 26, mounts to a wall, a ceiling, wall or floor carriage, an imaging system, or other location. The mounting is hinged or fixed. As another example, the support arm 26 mounts to the floor or ceiling, or a carriage. In another embodiment, the support arm is freestanding.

In one embodiment, the support arms 14, 18, 20, 26 are support structure similar to or also used for positioning dental, x-ray, or other equipment relative to a patient. Any now known or later developed support structure may be used. In another embodiment, the support structure is robotic. One or more motors move the support structure or portions of the support structure.

The brake 30 is a brake pad, detent structure, pin, gear, motor, or other device for releasably locking the relative position of the links and/or hinges 24. A motor, such as a servo, may be provided to engage and disengage the brake 30. Alternatively or additionally, the brake 30 is engaged and disengaged manually. In one embodiment, the brake 30 is a valve, pin, or other structure for locking the resistive device 16, 22. For example, a moveable pin causes a gas spring to lock.

The brake 30 maintains the relative position of links. For example, the brake 30 maintains a relative position of the support arm 20 to the support arm 26 and hinge 24/support arm 14. The brake 30 is a link holder operable to maintain one or more of the links in a stable position. The brake 30 locks the position of one or more support arms 14, 18, 20, 26.

The brake 30 is shown at the end of the support arm 20 adjacent the hinge 30. Other brakes are positioned at other locations, such as at other hinges (e.g., joints) or relatively moveable locations. One or more joints may be free of a brake 30. For example, the support structure includes the brake 30 for locking a position of a hinge 24 or support arm 20 while another support arm 14 is not locked or free to move as allowed by the resistive device 16 for applying pressure.

The resistance devices 16, 22 are springs, gas springs, pressure pads, friction surfaces, or other devices for resisting gravity and/or movement. One or more resistance devices 16, 22 are provided for each link. Alternatively, one or more links may share a resistance device 16, 22. The resistance devices 16, 22 are adjacent to the links, but may be within, on, or spaced from the links.

The resistance devices 16, 22 counteract the effects of gravity on all or portions of the support structure, acting as link holders. For example, the support arm 26 includes a pneumatic cylinder or gas spring for countering the gravity force acting on the rest of the support structure and ultrasound transducer 12. The resistance is substantially in equilibrium with the weight of the entire support structure supported by the support arm 26. Substantially allows for tolerance such that the resistance device may slowly (e.g., over minutes or hours) lift the support structure or may slowly lower due to weight when not locked. As another example, the resistance device 22 is substantially in equilibrium with the weight from the support arm 20 and other components connected between the support arm 20 and the ultrasound transducer 12. The resistance is sufficient to counter the effects of gravity. In another example, the resistance device 16 counters the weight of the support arms 14, 18 and ultrasound transducer 12.

One or more resistance devices 16, 22, 26 may be mistuned. For example, the resistance device 16 on the main support arm 14 closest to the ultrasound transducer 12 is mistuned. As another example, the resistance device in the base support arm 26 is mistuned. The base support arm 26 provides movement in up-down directions without rotation away from vertical in one embodiment. The gas spring or gas shock used in the base support arm 26 may be locked and/or mistuned. In other examples, two or more resistance devices 16, 22 are mistuned to act in concert to provide pressure for scanning.

The mistuning includes adjustment, sizing, or selection to be not in equilibrium. Less than all of a force from gravity applied to the support arm is counteracted. Due to the mistuning, gravity causes the ultrasound transducer 12 to press against an object for scanning or move downward when not contacting the object. The mistuning may allow movement between extremes in the range of available movement over a few minutes or less. The mistuning may allow pressure of three or more pounds, depending on the size of the object to be scanned or other considerations. The mistuned resistance device 16 counteracts some of the effects of gravity so that a pressure due to gravity of the transducer 12 against the patient 28 is less than caused by the force from gravity applied to the support arm without the resistance device 16. When the rest of the support structure is locked, the mistuned resistive device 16 allows pressure on the patient 28 or downward motion of the ultrasound transducer 12. Motion in other directions is locked or prevented by gravity.

The pressure is applied free of feedback from a pressure sensor. The mistuning alone allows application of the pressure. For example, during a power outage, the unlocked but mistuned resistive device 16 allows movement of the support arm 14. The sonographer or patient 28 merely applies sufficient force to lift the ultrasound transducer 12 with the assistance of the resistive device and against gravity. Alternatively, one or more motors are used with or without pressure sensors to apply the desired amount of pressure. During a power outage, such motor driven and sensed pressure may not operate, resulting in locking of the support arm 14.

Figure 2:
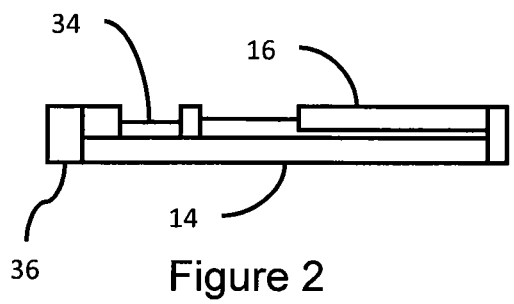
FIG. 2 illustrates an adjustable applicator for altering an amount of resistance according to one embodiment.

The amount of resistance provided by the resistive devices 16, 22 is set at the time of manufacture, installation, calibration, or during use. In one embodiment, the resistive devices 16, 22 have fixed resistance. In other embodiments, the resistance is adjustable. FIG. 2 shows one embodiment of an adjustable force applicator 34. The resistive device 16 applies a same amount of resistive force. By moving the adjustable force applicator 34, different amounts of weight counteracting force are applied. For the adjustable force applicator 34, a stepper motor and screw drive, belt drive, or other device reposition the base plate. A mechanical spring connects the base plate and the drive, allowing compaction or extension of the mechanical spring. The compaction or extension results in more or less force being applied by the adjustable force applicator 34. An optical sensor or motor sensor detects the position of the spring or plate for setting the desired resistance. The resistive device 16 and the adjustable force applicator 34 are shown in a series connection, but may be connected in parallel. Other structures may be used. The amount of resistance to the motion of the link may be altered. The amount of resistance is altered in installing, using, or calibrating the support structure.

In one embodiment, the amount of resistive force is adjusted during use. For example, less or more gravity force is applied depending on the angle of the support arm 14. If the support arm 14 is horizontal, more gravity force is to be resisted by the resistive device 16. If the support arm 14 is vertical, then little or no gravity force is resisted by the resistive device 16. Instead, the hinge 24, resistive device 22, and brake 30 counter the gravity.

A joint sensor 36 detects the angle. The joint sensor 36 is an optical sensor, angle sensor, motor sensor, or other sensor for determining an angle of the support arm 16. The angle information is fed back to a controller for selecting the position of the adjustable force applicator 34. The adjustable resistance is adjusted as a function of an angle of the support arm 14 relative to a direction of the force from gravity so the pressure is substantially constant regardless of the angle. The amount of resistance is adjusted as a function of the angle. Any desired range of pressures may be provided. The number of discrete adjustment positions of the adjustable resistance applicator 34, given the possible angles and mass, may determine the range of pressures applied by the ultrasound transducer 12 to the patient 28. For example, the amount of resistance is adjusted or is set to provide 5-15 pounds of force. Greater, lesser, or different ranges may be provided. The lesser of the pressures should be sufficient to allow scanning contact for the ultrasound transducer 12 even with breathing or other motion. The greater of the pressures should avoid discomfort of the patient 28. A sensor, mechanical limiter, or other control may prevent exceeding a particular pressure. A feedback sensor may be provided for preventing unsafe pressures. Alternatively, no feedback sensor is used.

Figure 3:
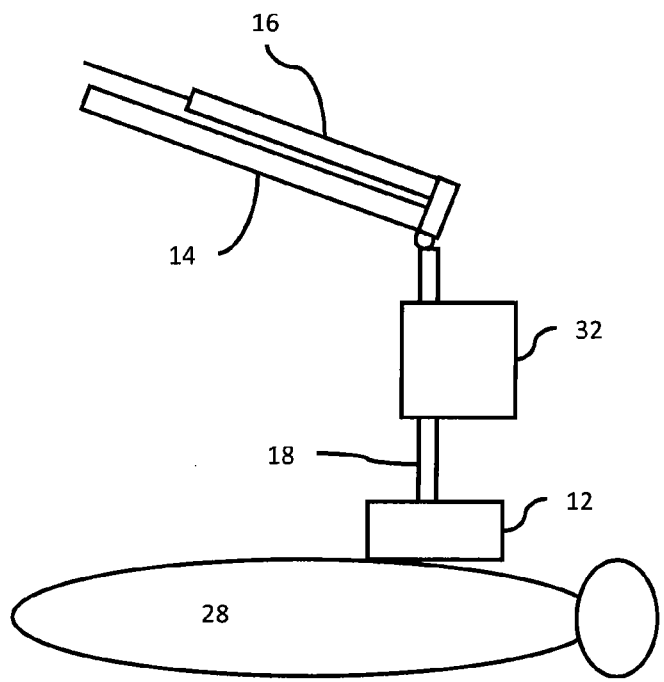
FIG. 3 illustrates another embodiment of a system for ultrasound scanning with a monitor on a support structure.

Other components may be added to the support structure. For example, FIG. 3 shows a monitor 32 connected with the support arm 18. The monitor 32 may connect with different or additional links. The monitor 32 is a CRT, LCD, or other display device for displaying medical images. For example, the ultrasound transducer 12 scans the patient. An ultrasound system generates one or more images of the scanned region. The images are displayed on the monitor 32, providing the images at a location more easily viewed by the sonographer.

Figure 4:
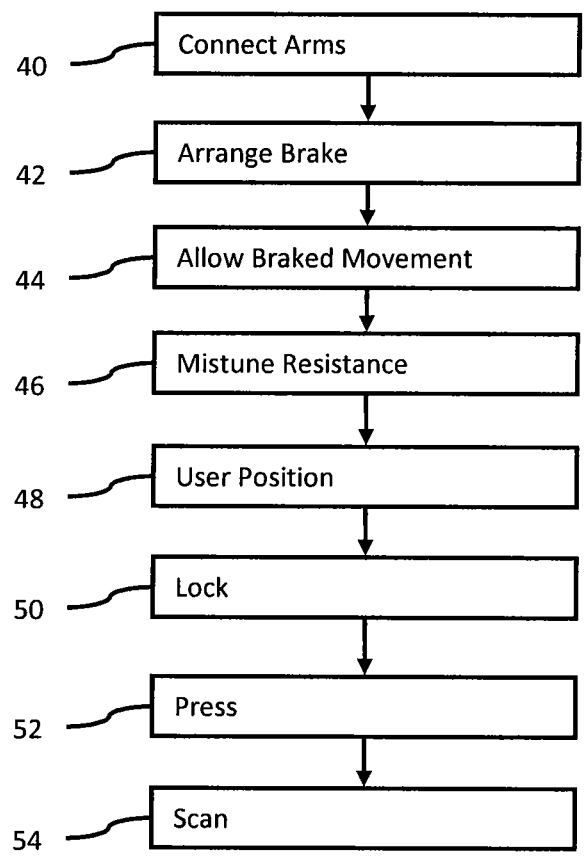
FIG. 4 is a flow chart diagram of one embodiment of a method for supporting an ultrasound transducer and using the supported transducer.

FIG. 4 shows a flow chart diagram for one embodiment of a method for supporting an ultrasound transducer. The method is implemented with the structural supports of FIGS. 1-3 or different structural supports. The acts are performed in the order shown or different orders. Acts 40-46 generally correspond to manufacture of the structural support, and acts 48-54 generally correspond to use of the structural support. Acts 40-46 may be performed without acts 48-54, or vice versa. Additional, different, or fewer acts may be provided. For example, the mistuned resistance of act 46 is provided without the arranging brakes and braking of acts 42 and 44. As another example, a computer positions rather than a user in act 48.

In act 40, arms of an ultrasound transducer support structure are connected. The connections may be direct or indirect. Any joint, hinge or other type of connection may be used. The connection is snap fit, bolted, screwed, latched, or any other type of combination.

Any number of arms may be connected. The connections form the support structure. The arms are connected so that an ultrasound transducer connected to the ultrasound transducer support structure may be supported in any position in a patient area.

In act 42, at least one brake is arranged on the support structure. Brakes are added as the support structure is assembled. For example, a brake is provided for each degree of freedom other than up and down on each arm. Some or all of the arms may include brakes for up and down motion as well. The brakes may be integrated in the arms or added separately. For example, a gas spring with a lock tab is connected in parallel with an arm. Any type of connection may be used to fix the brakes to the support structure.

The brakes are positioned on the support structure to lock the ultrasound transducer support structure in a position to scan a patient. Depending on the degrees of freedom for a given joint or arm and motion mechanism, one or more brakes may be positioned to prevent motion. The brakes may be connected with control wires, sensors, and/or controllers.

In act 44, at least one portion of the ultrasound transducer support structure is allowed to move. The support structure and brakes are arranged so that, even when locked by the brakes, a portion of the support structure may move along at least one degree of freedom (rotation and/or translation). For example, one arm is allowed to move vertically while the ultrasound transducer support structure is locked. The vertical movement may be through rotation or translation. Any components or portions supported by the moving portion may also move. The movement is free or restricted. The restriction may be due to countering force, friction, or limiters (e.g., a plate preventing movement beyond a certain extent).

In one embodiment, the braked movement is allowed by not locking one of the brakes or not providing a brake. For example, a gas spring along one arm is not locked while other gas springs along other arms or even the same arm are locked. The brake may be locked for other purposes.

In act 46, a resistance to gravity is mistuned. The ability of the portion to move is resisted, but not halted, through at least a range of rotation or translation. Gravity acting on the portion and any supported components causes the transducer to press against the patient. The effects of gravity are resisted, but not fully countered. For example, a gas spring resists the motion in a way insufficient to hold the one portion in place without the patient during scanning (i.e., while the portion is in the air and not resting against something). Resistance is provided, but not enough to prevent gravity induced pressure or movement. Any resistance may be used, such as friction, pressure, motor driven, elastic, or mechanical resistance.

Allowing braked movement of a portion of the support structure and mistuning equilibrium resistance result in the support structure holding the transducer against the patient during scanning. The locking prevents undesired motion, such as lateral motion. If the patient moves (e.g., breathing during a chest scan), the resulting force from the patient may act to lift the support structure. However, gravity maintains a substantially same pressure regardless of the patient's motion. Substantially is used to account for the effects of acceleration and tolerance. The pressure is provided without more complex feedback sensing and robotic control. Feedback sensors may be used in other embodiments or to assist in the maintenance of the desired pressure.

In act 48, the assembled support structure is used by a sonographer. The ultrasound transducer is positioned by the user. The user applies force to the transducer and/or the support structure. The user positions the support structure and the transducer. The transducer is positioned adjacent the patient, such as over or against a breast of the patient. In alternative embodiments, force applied by motors or other sources than the user positions the ultrasound transducer.

During positioning, the support structure generally maintains equilibrium with gravity. The user applies force to overcome this equilibrium or other friction. The mistuned portion may be mistuned during positioning. The user counteracts or adds to the gravity force to position the mistuned portion. Alternatively, the mistuned portion is adjustable so that during positioning or not during use, the portion is held in equilibrium.

In act 50, the ultrasound transducer support structure is locked. Brakes are applied, such as mechanical limiters positioned to prevent motion. The user activates a switch. In response, a controller causes the brakes to activate. For example, servo or stepper motors position brake pads against a surface, engage gear locks, freeze joint motors, adjust pins, or perform another action to lock the brakes. Alternatively, the user manually locks one or more brakes. In other embodiments, locking is not provided. Instead, the equilibrium is used. The resistance to gravity or other motion holds the support structure sufficiently in place. Any motion upward may be countered by downward motion of the mistuned portion.

In act 52, the ultrasound transducer presses against the patient. For example, the transducer presses against the breast. The pressure is applied passively, such as without motors.

The pressure is of any amount. The pressing is caused by mistuning the resistance to gravity. Some resistance is provided to limit the pressure applied to the patient. The portion of the support structure moveable while the rest of the support structure is locked or in equilibrium applies the pressure.

With an adjustable resistance, the locking of act 50 may cause adjustment of the resistance. This activates the mistuning for use. Alternatively, the mistuning exists even when not being used for scanning. The support arm is stowed in a manner that prevents movement of the mistuned portion, such as resting the mistuned portion against a limiter or in a vertical position.

In act 54, the patient is scanned with the ultrasound transducer. Transmit waveforms are applied to the transducer. The transducer converts the waveforms into acoustic energy. Echoes from the acoustic energy are received by the transducer and converted into electrical energy. Using an array of elements and/or mechanical movement of a transducer, a two or three-dimensional region of the patient may be scanned. For example, a breast volume of a patient is scanned. To avoid acoustic interference, the transducer is maintained against the patient during the scan. The constant pressure from the mistuning applies sufficient pressure to maintain the contact for scanning.

An image is generated using the received electrical signals. Using beamforming, data representing different locations is generated. The data is scan converted or rendered to generate a two dimensional image representing a plane or a rendered volume. The image is displayed on a monitor available to the sonographer, such as a monitor on the support arm.

In another embodiment, the transducer holder has a mechanized scan system. The mechanized scan system, such as a wobbler or linear movement of a one-dimensional array, moves an array to carry out a 3-dimensional scan. The ultrasound system receives the electrical signals and processes and displays 3-dimensional images on screen. The arm locking mechanism holds the arm support in place and avoids undesirable motion during the scan duration (e.g., 60-120 seconds).

After scanning, the sonographer may unlock the system and reposition the transducer holder. In another embodiment, the mistuning is adjusted when the scan is complete. Scan completion is indicated by the user unlocking the arms, other user input, or completion of the 3D scan. In response, the mistuning is reversed. The resistance is increased to more than overcome gravity. As a result, the support arm and transducer move upward, away from the patient. This may allow sufficiently high placement of the transducer for freedom of movement by the patient without requiring the sonographer to reach the desired height of clearance.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A system for ultrasound scanning, the system comprising:
   an ultrasound transducer;
   at least a first support arm connected with the ultrasound transducer, the first support arm being moveable;
   a resistance device configured to counteract less than all of a gravitational force applied to the first support arm, such that gravity causes the ultrasound transducer to press against an object for scanning with a pressure less than caused by the gravitational force applied to the first support arm without the resistance device but more than zero;
   an adjustable resistance applicator configured to apply different amounts of weight counteracting force;
   a joint sensor configured to detect an angle of the first support arm or another support arm;
   a controller in communication with the joint sensor, the controller configured to:
      determine an angle of the first support arm or the other support arm relative to the direction of the gravitational force based on the detected angle; and
      adjust an amount of resistance provided by the resistance device and the adjustable resistance applicator based on the determined angle such that the pressure with which the ultrasound transducer is pressed against the object is maintained.

2. The system of claim 1 wherein the first support arm is moveable in an up and down direction.

3. The system of claim 1 wherein the resistance device comprises a gas spring.

4. The system of claim 1 wherein the resistance device comprises a spring.

5. The system of claim 1 wherein the pressure is applied free of feedback from a pressure sensor.

6. The system of claim 1 further comprising: a second support arm connected with the first support arm, the connection of the second support arm to the first support arm being rotatable about an axis of the second support arm, hinged, or both rotatable and hinged.

7. The system of claim 6 further comprising: a brake configured to lock a position of the second support arm while the first support arm is operable to apply the pressure.

8. The system of claim 7 wherein the first support arm is moveable during a power failure while the second support arm is locked.

9. The system of claim 7, wherein the brake is a brake pad, detent structure, pin, gear, motor, or valve.

10. The system of claim 1 further comprising: a monitor connected with the first support arm, the monitor operable to display an image of the object obtained with the ultrasound transducer.

11. The system of claim 1, wherein the pressure with which the ultrasound transducer is pressed against the object is between 5 and 15 pounds-force per square inch.

12. The system of claim 1, wherein the adjustable resistance applicator is a stepper motor and a screw drive or a belt drive.

* * * * *